United States Patent
Bazzano

Patent Number: 5,721,275
Date of Patent: Feb. 24, 1998

[54] SLOW RELEASE VEHICLES FOR MINIMIZING SKIN IRRITANCY OF TOPICAL COMPOSITIONS

[76] Inventor: Gail S. Bazzano, 4506 Avron Blvd., Metairie, La. 70006

[21] Appl. No.: 856,157
[22] PCT Filed: Jun. 7, 1990
[86] PCT No.: PCT/US90/03219
§ 371 Date: Jan. 21, 1992
§ 102(e) Date: Jan. 21, 1992
[87] PCT Pub. No.: WO90/14833
PCT Pub. Date: Dec. 13, 1990
[51] Int. Cl.$^6$ ............................ A61K 31/20; A61K 31/78
[52] U.S. Cl. ..................... 514/559; 514/859; 514/944; 424/78.02
[58] Field of Search ............................ 514/859, 944, 514/559

[56] References Cited

U.S. PATENT DOCUMENTS

| | | | |
|---|---|---|---|
| 3,729,568 | 4/1973 | Kligman | 514/859 |
| 3,906,108 | 9/1975 | Feltig | 514/559 |
| 4,021,573 | 5/1977 | Lee | 514/863 |
| 4,214,000 | 7/1980 | Papa | 514/559 |
| 4,247,547 | 1/1981 | Marks | 514/559 |
| 4,950,475 | 8/1990 | Vishnupad et al. | 514/944 |

FOREIGN PATENT DOCUMENTS

| | | |
|---|---|---|
| 0010208 | 4/1980 | European Pat. Off. . |
| 0274104 | 7/1988 | European Pat. Off. . |
| 2187340 | 1/1974 | France . |
| 2247203 | 5/1975 | France . |
| 2309448 | 9/1973 | Germany . |
| 906000 | 9/1962 | United Kingdom . |

OTHER PUBLICATIONS

The Merck Index, 1976, Ninth Edition, p. 7961 Published by Merck & Co, Ind. Rahway, N.J., U.S.A..

*Primary Examiner*—C. Warren Ivy
*Assistant Examiner*—Evelyn Huang
*Attorney, Agent, or Firm*—Panitch Schwarze Jacobs & Nadel, P.C.

[57] ABSTRACT

Staple, aqueous gel vehicles are provided for the topical application to the skin of irritating active ingredients such as retinoids, particularly tretinoin, with slow release of the active ingredient and minimal irritancy to the skin. The vehicles include a gelling agent effective to form a gel and hold the active ingredient in the aqueous medium for slow release on the skin, and an effective amount of an antioxidant to retard decomposition of the active ingredient. The vehicles and formulations are preferably aqueous emulsions which contain a solubilizing agent for the generally non-water soluble active ingredients, as well as usually an emulsifying agent and/or surfactant. Chelating agents, emollients, preservatives and other adjuvants and additives may also be included in the vehicles and formulations.

15 Claims, No Drawings

SLOW RELEASE VEHICLES FOR MINIMIZING SKIN IRRITANCY OF TOPICAL COMPOSITIONS

This application is the national share of PCT/US90/03219, filed Jun. 9, 1990, U.S. Ser. No. 07/362529, filed Jun. 7, 1989 abandoned and Ser. No. 07/429051, filed Oct. 30, 1989, abandoned.

FIELD OF THE INVENTION

The invention relates to stabilized, slow-release vehicles for normally irritating, non-water soluble active ingredients for topical application to the skin. More particularly, the invention is directed to aqueous emulsion formulations of retinoids for topical application to individuals who are sensitive to retinoids in other vehicles.

BACKGROUND OF THE INVENTION

Topical retinoids have been widely used for multiple cutaneous disorders, as reported in A. Haas et al. "Selected Therapeutic Applications of Topical Tretinoin," *JAAD*, 15:870 (1986) (See Table I below). In many instances, the application of tretinoin has alleviated or induced remission in many such conditions, although these disorders reflect a variety of pathogenic mechanisms.

TABLE I

Selected Therapeutic Application of Topical Tretinoin

Disorders with altered keratinization

Acneiform follicular, or nevoid

Nevus comdeonicus
Senile comedones
Steroid folliculitis
Pseudofolliculitis
Fox-Fordyce disease
Hair casts
Monilethrix
Alopecia
Thrichiostasis spinulosa
Linear verrucous nevus
Ichthyosiform Epidermolytic hyperkeratosis
(congenital ichthyosiform erythroderma)
Ichthyosis vulgaris
Lamellar ichthyosis
X-linked ichthyosis
Psoriasiform, hyperkeratotic, or dyskeratotic Acanthosis and pseudoachanthosis nigricans
Callosites
Keratosis follicularis (Darier's)
Keratosis palmaris et plantaris
Kyrle's disease
Psoriasis
Reactive perforating collagenosis
Infectious/inflammatory disorders Molluscum contagiosum
Flat warts
Plantar warts
Tinea versicolor
Leg ulcers
Keloids and hypertrophic scars

TABLE I-continued

Selected Therapeutic Application of Topical Tretinoin

Mucocutaneous disorders

Geographic tongue
Lichen planus
Leukoplakia
Xerophthalmia (dry eye)
Hairy leukoplakia
Pigmentation disorders Ephelides
Melasma
Postinflammatory hyperpigmentation
Malignant and premalignant disorders Actinic keratoses, photoaging
Keratoacanthomas
Melanomas
Certival dysplasis
Basal cell epithelioma It has been demonstrated that prolonged topical application of Vitamin A acid (tretinoin or all-trans retinoic acid) is effective in the treatment of acne (See U.S. Pat. No. 3,729,568 and Kligman, A. M., "Topical Vitamin A Acid in Acne Vulgaris," *Arch. Derm.*, 99: 469–476 (1969)). Kligman utilizes a composition in which Vitamin A acid is dispersed in a water miscible (substantially oil- and fat-free) liquid carrier having high solvating action. The topical application of this Vitamin A acid composition causes irritation of the skin in the treated areas. A presently available gel form with alcohol base or cream formulation also causes irritation. (See U.S. Pat. Nos. 3,906,108 and 4,247,547.)

A cream formulation of tretinoin is presently approved and is commercially available from Ortho Pharmaceutical Company under the trademark RETIN-A. It contains a therapeutically effective amount of tretinoin, a hydrophobic material selected from the liquid and solid fatty acids, fatty alcohols, fatty acid esters, pharmaceutical grades of waxes and hydrocarbons, the latter ranging from liquids through semisolids, such as petrolatum, to solids, and the like, a non-ionic emulsifier, xanthan gum, a preservative, an antioxidant and water. This formulation is more generally acceptable in a low dose 0.025% formulation, but it is still unacceptable to certain individuals with sensitive skin for continued daily applications.

Furthermore, the above tretinoin cream is relatively dense and pasty, and the pharmaceutical base is not elegant. The necessity to stabilize the cream with xanthan gum and to apply daily or twice daily a fatty substrate to the skin leaves a greasy film with a pasty residue.

Therefore, the problem has been to find vehicles for retinoids, particularly tretinoin, and other irritating active ingredients in which the active ingredient would remain stable and non-oxidized in the presence of large amounts of water, while dramatically reducing the amount of irritation caused by the active ingredient. It is also desirable to have a vehicle which can provide sufficient hydration to allow good percutaneous absorption, while at the same time allowing the active ingredient to be spread very thinly over the skin.

BRIEF SUMMARY OF THE INVENTION

According to the present invention, stable, aqueous retinoid formulations are provided for topical application to the skin, with slow release and stability of the retinoid and minimal irritancy to the skin. The formulations comprise an aqueous medium, an amount of retinoid effective for treatment of a skin condition, a gelling agent in an amount effective to form a gel and hold the retinoid in the aqueous medium for slow release, and an antioxidant to retard decomposition of the retinoid in the aqueous medium. The formulations are particularly adapted for use with tretinoin and dermatologically acceptable salts, isomers and derivatives thereof, and the gelling agent is preferably a high molecular weight polyacrylic acid which is neutralized to a pH of about 3 to 7.

In addition to the above ingredients, the formulations of the invention preferably also include a solubilizing agent for the retinoid, a non-ionic emulsifying agent to form a stable emulsion of the retinoid in the aqueous medium, a lipophilic agent which may serve as an emollient, and a chelating agent to assist in holding the retinoid for slow release. Surfactants, preservatives and other suitable additives may also be included. Moreover, the aqueous emulsion vehicles according to the present invention may also be used for the topical application of other normally irritating, non-water soluble active ingredients besides retinoids.

DETAILED DESCRIPTION OF THE PREFERRED EMBODIMENTS

According to the present invention, it has been found that vehicles described herein can be used very effectively in order to prevent and retard the amount of irritation caused by topically applied retinoids. These vehicles allow good percutaneous absorption and at the same time provide a very high degree of hydration without causing oxidation of the retinoid molecule. The use of a slow-release vehicle based on a polyacrylate gelling agent in an aqueous medium is surprising because it has been thought previously that gels containing a high degree of water would cause great instability in the retinoid molecule. Also, it was thought that a gel formulation containing water as a primary base would lead to residues of retinoid aggregating on the skin without allowing percutaneous absorption, thereby leading to an inactive retinoid product which would readily oxidize on the skin.

I have discovered that surprisingly the gelling agent actually acts as a compound which allows stabilization of the retinoid and slowly releases it so that it can optimally feed into the keratinocyte layers and dermal cells of the skin.

The vehicles and formulations of the present invention are particularly useful to patients who are sensitive to irritating active ingredients, particularly retinoids such as tretinoin. Thus, the slow-release vehicle provides a great improvement in skin comfort and ease of application and reduces the side effects normally associated with topical application of such active ingredients. The side effects, including erythema, stinging, peeling, crusting, and itching, may be sufficient to cause the patient to discontinue the application of the active ingredient before it can be fully effective. Furthermore, the vehicles of the invention are more cosmetically acceptable and leave no residues of fatty or sticky substances on the skin surface.

While the present invention is believed to be broadly applicable to a variety of normally irritating active ingredients for topical application to the skin, and particularly to non-water soluble active ingredients, the invention has been found to be particularly useful for the topical application of retinoids, particularly tretinoin, and the following description will therefore be particularly directed to vehicles and formulations which have been designed for and tested with tretinoin. However, it will be understood that the broad teachings of this disclosure are applicable to other retinoids, and may be applicable to other normally irritating active ingredients for topical treatment of the skin.

As used in the present invention, the terms "aqueous" and "aqueous medium" are intended to refer to vehicles and formulations in which the major liquid component is water. Generally speaking, such vehicles and formulations will comprise at least 40% to 50% water and usually more. Thus, the vehicles and formulations of the present invention are to be distinguished from formulations in which the major or primary liquid is an alcohol or other organic solvent.

The gelling agents useful in the present invention are those which form a gel in aqueous medium and hold the retinoid for slow release while allowing the active ingredient to be spread over the skin in a thin, uniform layer while maintaining the integrity of the retinoid molecule. Particularly preferred gelling agents useful in the present invention are the high molecular weight polyacrylate polymers (CAS 9003-01-4) and related polymers which are known agents for use in various types of pharmaceutical and cosmetic compositions. These polyacrylates are formed by neutralizing polyacrylic acids with a base, such as sodium hydroxide or an amine, to an acid pH in the range of about 3 to 7. The neutralization with a base causes the polyacrylic acid to swell (hydrate) to a gel.

Examples of commercially available polyacrylate gelling agents include those sold under the trademark "CARBOPOL", available from the B. F. Goodrich Company. The CARBOPOL polymers have high molecular weights ranging from about 250,000 to about 4,000,000. The viscosity of the final gel is dependent on the polymer molecular weight, as well as the concentration of the polymer in the vehicle or formulation. The gelling agent should be present in an amount of about 0.1 to 10 weight percent, depending upon the thickness of the gel desired.

Particularly preferred in the vehicles and formulations of the present invention is CARBOPOL 940 (pharmaceutical grade) which has molecular weights in the range of about 3,000,000 to 4,000,000. This gelling agent is preferably used in an amount of about 0.2 to 0.5 weight percent of the formulation or vehicle. Of course, it will be understood that other CARBOPOL resins such as CARBOPOL 941, CARBOPOL 934P, etc., as well as other polyacrylates and other comparable gelling agents, may be used in the vehicles and formulations of the present invention. In general, the use of different molecular weight polyacrylates will only affect the degree of viscosity obtained.

It has been found according to the invention that the polyacrylate gelling agents have the surprising characteristic of retaining the readily oxidizable retinoid compounds in a protected state, exposed optimally only to the antioxidant. The gelling agent also efficiently spreads the retinoid in a very fine layer over the stratum corneum, which allows percutaneous absorption without excessive spots of retinoid to cause skin reaction and irritation, which have been commonly seen with the fatty substrates and gummy substances presently used as vehicles for retinoid application.

The active ingredients which are applied with the vehicles according to the present invention are preferably retinoids which are commonly used for the treatment of various skin conditions, such as those described above. More particularly, the active ingredient is the commonly used retinoid tretinoin (Vitamin A acid or all-trans retinoic acid), and its effective, dermatologically acceptable salts, isomers and derivatives thereof, such as isotretinoin (13-cis-retinoic acid). However, as indicated above, other retinoids and other similarly irritating active ingredients may be used in the vehicles of the present invention to form dermatological compositions for topical treatment of the skin. The retinoid will generally be present in the formulation in an amount of about 0.01 to 0.1 weight percent of the formulation, and preferably about 0.01 to 0.05 weight percent. However, the amount of retinoid or other irritating active ingredient may vary depending upon the strength of the retinoid and the particular condition being treated.

Since the retinoid is more susceptible to oxidation and resulting decomposition when present in an aqueous medium, the vehicles of the present invention must contain an antioxidant in proportion to the retinoid content. That is, the higher the concentration of the retinoid, the more antioxidant which will be required. Generally, the antioxidant should be present in an amount of about 0.01 to 4 weight percent of the formulation. Suitable antioxidants include dl-alpha-tocopherol, butylated hydroxyanisole (BHA), butylated hydroxytoluene (BHT), ascorbyl palmitate and propyl gallate, for example. Other suitable antioxidants for retinoids will be readily recognized by those skilled in the art.

In addition to the above ingredients, the vehicles and formulations of the present invention may optionally contain other agents and additives which assist in the purposes of the present invention or which are conventionally used in topical dermatological compositions. Since retinoids are generally non-water soluble, it is generally preferred to first dissolve (solubilize) the retinoid in a solvent (solubilizing agent) for the retinoid. In the case of tretinoin, ethanol, isopropanol or another non-ionic alcohol in an amount of about 1 to 20 weight percent of the formulation may be used to first solubilize the retinoid. Thereafter, the alcohol-solubilized retinoid may be combined with an emulsifier in order to form an emulsion in the aqueous medium. The emulsifier is preferably at least one normally liquid glycol, preferably propylene glycol, which may be present in the formulation in an amount of about 1 to 20 percent by weight.

When using a solubilizing agent and/or emulsifier, the formulations of the invention are preferably formed by first dissolving the retinoid in the solubilizing agent and combining with the emulsifier and any other organic, lipophilic ingredients. In a separate vessel, the gelling agent is added to water and then neutralized to swell the gel. Thereafter, the solubilized active ingredient and lipophilic agents are added to the swelled gel and mixed to form the final gel emulsion. It will be recognized, however, by those skilled in the art that other methods and means of emulsifying the active ingredient in the aqueous gel may be employed consistent with the teachings of the present invention.

In order to assist the gelling agent in providing the slow release of the retinoid, the formulations of the invention may also include a suitable chelating or sequestering agent, preferably in an amount of up to about 0.5% by weight of the formulation. Suitable chelating agents include, for example, sodium and calcium salts of EDTA, such as disodium EDTA and calcium disodium EDTA.

Further, it may be desirable to include a surfactant as one of the components of the vehicle. Thus, the inclusion of a surfactant may have the dual benefit of helping to maintain the active ingredient in uniform suspension in the formulation, while enhancing the bio-availability of the active ingredient. The surfactant may be present in an amount up to about 20% by weight of the formulation, and may include for example, lecithin; sorbitan monoesters, such as sorbitan monoleate, sorbitan monolaurate, sorbitan monopalmitate, sorbitan monostearate; polysorbates, such as those prepared from lauric, palmitic, stearic and oleic acids; polysorbate 20, mononylphenyl ethers of polyethylene glycols, such as the monoxynols; polyoxyethylene monoesters, such as polyoxeethylene monostearate, polyoxyethylene monolaurate, polyoxyethylene monoleate; dioctyl sodium sulfosuccinate; sodium lauryl sulfate; and polyoximers having a molecular weight between 2,000 and 8,000; triethanolamine; and ureas such as diazolidinyl urea. Preferably, a non-ionic surfactant is used if the stability of oxidizable ingredients in the formulation is affected by the ionic strength of the formulation.

Further, the formulations may contain up to about 10 weight percent of a lipophilic or hydrophobic agent, which may serve as an emollient or anti-irritant, as an additional help in relieving any irritation caused from the retinoid. Examples of such lipophilic agents include fatty materials such as fatty alcohols of about 12 to 20 carbon atoms, fatty acid esters having about 12 to 20 carbon atoms in the fatty acid moiety, petrolatum, mineral oils, and plant oils such as soybean oil, sesame oil, almond oil, aloe vera gel, and allantoin.

The formulations and vehicles of the present invention may further contain about 0.05 to 2 weight percent of a preservative or anti-microbial or anti-bacterial agent which prevents bacterial or microbial growth in the gel. Preferred preservatives include the parabens, preferably methyl paraben and ethyl paraben, and sorbitol. However, other conventional preservatives commonly used in pharmaceutical compositions will be readily recognized by those skilled in the art.

Finally, the vehicles and formulations of the present invention may optionally contain minor amounts of such other commonly used cosmetic adjuvants or additives as dyes, perfumes, sunscreens, etc., as will be readily recognized by those skilled in the art. In addition, it is also contemplated that the compositions of the invention may contain other topical active medicaments such as vitamins, lipids, hormones or anti-inflammatory agents, such as corticosteroids.

The invention will now be illustrated in more detail with reference to the following specific, non-limiting examples. The following formulation examples were tested for their particular effectiveness in preventing the oxidation of tretinoin. The formulations may contain varying amounts of tretinoin, such as 0.01, 0.025 or 0.05 weight percent. The results of these tests are set forth in Table II below, which shows the percent decomposition of tretinoin in the formulation vehicle after 10 months. Additional decomposition results for formulatation Example 2 are set forth after Table II.

FORMULATION EXAMPLE NO. 1

| Ingredient | Weight Percent |
| --- | --- |
| CARBOPOL 940 | 0.4 |
| Ethanol | 3.0 |
| Propylene glycol | 3.0 |
| BHT | 0.015 |
| Parabens | 0.05 |
| Tetrasodium EDTA | 0.001 |
| Polyethylene glycol 400 | 0.05 |
| Triethanolamine | 0.05 |
| Water | q.s. to 100 |

-continued

| Ingredient | Weight Percent |
|---|---|
| All of the following Formulation Examples 2 through 7 contain the following components in addition to those listed: | |
| Parabens | 0.05% |
| Tetra-sodium EDTA | 0.001% |
| Polyethylene glycol 400 | 0.05% |
| Triethanolamine | 0.05% |

FORMULATION EXAMPLE NO. 2

| Ingredient | Weight Percent |
|---|---|
| CARBOPOL 940 | 0.50 |
| Propylene glycol | 1.00 |
| Ethanol | 2.00 |
| BHT | 0.015 |
| Water | q.s. to 100 |

FORMULATION EXAMPLE NO. 3

| Ingredient | Weight Percent |
|---|---|
| CARBOPOL 940 | 1.60 |
| Propylene glycol | 6.00 |
| Ethanol | 10.00 |
| BHT | 0.03 |
| Water | q.s. to 100 |

FORMULATION EXAMPLE NO. 4

| Ingredient | Weight Percent |
|---|---|
| CARBOPOL 940 | 0.4 |
| Propylene glycol | 20.0 |
| Ethanol | 20.0 |
| BHT | 0.01 |
| Water | q.s. to 100 |

FORMULATION EXAMPLE NO. 5

| Ingredient | Weight Percent |
|---|---|
| CATBOPOL 940 | 0.5 |
| Propylene glycol | 10.0 |
| Ethanol | 20.0 |
| BHT | 0.1 |
| Water | q.s. to 100 |

FORMULATION EXAMPLE NO. 6

| Ingredient | Weight Percent |
|---|---|
| CARBOPOL 940 | 0.4 |
| Propylene glycol | 3.5 |
| Isopropyl alcohol | 10.0 |
| BHT | 0.1 |
| Water | q.s. to 100 |

FORMULATION EXAMPLE NO. 7

| Ingredient | Weight Percent |
|---|---|
| CARBOPOL 940 | 0.3 |
| Propylene glycol | 1.20 |
| Isopropyl alcohol | 1.90 |
| BHT | 0.01 |
| Water | q.s. to 100 |

TABLE II

Stability Test Results

| Formulation Example No. | Percent Decomposition of Tretinoin (10 months) |
|---|---|
| 1 | 11 |
| 2 | 5 |
| 3 | 8 |
| 4 | 11 |
| 5 | 3 |
| 7 | 13 |

Formulation Example No. 2 was additionally tested for decomposition and found to have 2% decomposition of tretinoin after one month and about 13% decomposition of tretinoin after one year.

In order to test and demonstrate the effectiveness of the vehicles of the present invention in delivering retinoids in a less irritating manner while retaining therapeutic efficacy, the following studies were performed.

Animal Studies

In order to assess the bio-equivalency of tretinoin in an aqueous gel base according to the present invention, compared to the presently FDA approved formulation (RETIN-A), the Rhino mouse model was utilized. Thus, topical tretinoin produces a dose-dependent reduction in the size of the horn-filled utriculi in Rhino mouse epidermis. In this study, equivalent concentrations of tretinoin (0.025 weight percent) in the CARBOPOL gel formulation of Formulation Example No. 2 and in the RETIN-A cream vehicle were applied daily to the dorsal trunk skin of Rhino mice for up to two months. At two-week intervals, biopsies and photographs were taken to assess the effect of the tretinoin on histology, reduction of utriculi and general skin appearance. The resulting histology showed equivalent activity in the Rhino mouse epidermis treated with tretinoin in either the CARBOPOL gel formulation or the RETIN-A formulation.

Similar studies performed with Rhino mice skin at 0.05 percent and higher concentrations of tretinoin showed equivalent activity in both the CARBOPOL gel and RETIN-A formulations.

Clinical Studies

Seventy volunteer subjects participated in this study to assess the therapeutic efficacy as well as the irritancy potential of aqueous gel formulations of the present invention versus the RETIN-A cream formulation. These subjects had all previously reported that they could not use the presently available formulations of tretinoin without experiencing irritation sufficient to cause them to discontinue the use of the drug. Subjects were given either a 0.025% or 0.05% tretinoin formulation in the CARBOPOL gel formulation of Formulation Example No. 2 above and were asked to apply the gel twice daily. These subjects were followed for six months, and results were evaluated by the attending dermatologist as well as the patient.

Sixty-seven of the volunteers completed the study. As compared to the 100% irritation reported by these volunteers who had all previously used the commercial 0.025% tretinoin formulation of RETIN-A, only 10 reported irritation using the CARBOPOL gel formulation of Example 2 above. Of these, three reported mild irritation with the 0.025% gel formulation, six reported mild irritation with the 0.05% gel formulation, and only one reported moderate irritation with the 0.05% gel formulation. None of the subjects reported severe irritation with either concentration of the gel formulation.

These results demonstrate that the slow release CARBOPOL gel formulations of the present invention were less irritating than the standard RETIN-A cream formulation. Subjects sensitive to RETIN-A were able to tolerate equivalent and stronger concentrations of tretinoin in the gel formulation without as much irritation, and therefore they continued to use the tretinoin as prescribed.

Additional subjects have been tested in studies with 0.01% tretinoin in the gel formulations of the present invention, with similar results being obtained. In general, the slow release gel vehicles of the present invention appear to be an effective method of delivering tretinoin in a less irritating manner while still maintaining therapeutic efficacy.

The present invention may be embodied in other specific forms without departing from the spirit or essential attributes thereof and, accordingly, reference should be made to the appended claims, rather than to the foregoing specification as indicating the scope of the invention.

I claim:

1. A stable, aqueous retinoid composition for topical application to the skin with slow release of the retinoid and minimal irritancy to the skin, comprising:

(a) an aqueous medium such that the composition is at least about 40 weight percent water;

(b) an amount of retinoid effective for treatment of a skin condition;

(c) an amount of a high molecular weight polyacrylic acid gelling agent neutralized to a pH of about 3 to 7 effective to form a gel and hold said retinoid for slow release in said aqueous medium; and (d) an amount of antioxidant effective to retard decomposition of said retinoid in said aqueous medium.

2. A composition according to claim 1 comprising about 0.01 to 0.1 weight percent retinoid, about 0.1 to 10 weight percent gelling agent, about 0.01 to 4 weight percent antioxidant, and at least about 50 weight percent water.

3. A composition according to claim 1 wherein said retinoid is selected from the group consisting of tretinoin and effective, dermatologically acceptable salts, isomers and derivatives thereof.

4. A composition according to claim 1 wherein said antioxidant is selected from the group consisting of dl-alpha-tocopherol, butylated hydroxyanisole, butylated hydroxytoluene, ascorbyl palmitate, and propyl gallate.

5. A composition according to claim 1 which includes about 0.1 to 20 weight percent of a solubilizing agent for said retinoid.

6. A composition according to claim 5 wherein said solubilizing agent is ethanol.

7. A composition according to claim 1 which includes about 0.1 to 20 weight percent of a non-ionic emulsifying agent to form a stable emulsion of said retinoid in water.

8. A composition according to claim 7 wherein said emulsifying agent comprises at least one normally liquid glycol.

9. A composition according to claim 1 which contains a surfactant selected from the group consisting of lecithin, sorbitan monoesters, polysorbates, mononylphenyl ethers of polyethyleneglycols, polyoxyethylene monoesters, dioctyl sodium sulfosuccinate, sodium lauryl sulfate, polyoxamers having a molecular weight of 2000 to 8000, triethanolamine, and ureas.

10. A composition according to claim 1 which includes up to about 10 weight percent of a lipophilic agent.

11. A composition according to claim 10 wherein said lipophilic agent is selected from the group consisting of fatty alcohols of about 12 to 20 carbon atoms, fatty acid esters having about 12 to 20 carbon atoms in the fatty acid moiety, petrolatum, plant oils and mineral oils.

12. A composition according to claim 1 which contains about 0.05 to 2 weight percent of a preservative.

13. A composition according to claim 12 wherein said preservative is selected from the group consisting of methyl paraben, ethyl paraben and sorbitol.

14. A composition according to claim 1 which includes up to about 0.5 weight percent of a chelating agent for said retinoid.

15. A composition according to claim 14 wherein said chelating agent is selected from the group consisting of sodium and calcium salts of EDTA.

* * * * *